United States Patent [19]
MacLauchlan et al.

[11] Patent Number: 5,675,087
[45] Date of Patent: *Oct. 7, 1997

[54] FASTENER CHARACTERIZATION WITH AN ELECTROMAGNETIC ACOUSTIC TRANSDUCER

[75] Inventors: Daniel T. MacLauchlan, Lynchburg; Wayne M. Latham; Steven P. Clark, both of Forest, all of Va.

[73] Assignee: The Babcock & Wilcox Company, New Orleans, La.

[*] Notice: The term of this patent shall not extend beyond the expiration date of Pat. No. 5,499,540.

[21] Appl. No.: 594,051

[22] Filed: Jan. 30, 1996

Related U.S. Application Data

[63] Continuation-in-part of Ser. No. 196,917, Feb. 15, 1994, Pat. No. 5,499,540.

[51] Int. Cl.$^6$ .................................................. F16B 31/02
[52] U.S. Cl. ............................. 73/761; 73/597; 73/601
[58] Field of Search ............................ 73/761, 597, 601, 73/622, 623

[56] References Cited

U.S. PATENT DOCUMENTS

| | | | |
|---|---|---|---|
| 4,434,663 | 3/1984 | Peterson et al. | 73/643 |
| 4,522,071 | 6/1985 | Thompson | 73/597 |
| 4,710,710 | 12/1987 | Flora et al. | 73/866.5 |
| 4,777,824 | 10/1988 | Alers et al. | 73/643 |
| 4,846,001 | 7/1989 | Kibblewhite | 73/761 |
| 4,856,337 | 8/1989 | Metala et al. | 73/623 |
| 5,050,703 | 9/1991 | Graff et al. | 73/643 |
| 5,058,439 | 10/1991 | Carpenter | 73/761 |
| 5,154,081 | 10/1992 | Thompson et al. | 73/597 |
| 5,178,005 | 1/1993 | Peterson | 73/597 |
| 5,220,839 | 6/1993 | Kibblewhite | 73/761 |
| 5,343,785 | 9/1994 | Holt et al. | 73/761 |
| 5,396,800 | 3/1995 | Drinon et al. | 73/623 |
| 5,499,540 | 3/1996 | Whaley et al. | 73/761 |

FOREIGN PATENT DOCUMENTS

| | | | |
|---|---|---|---|
| 55134331 | 10/1980 | Japan | 73/761 |
| 63-286761 | 11/1988 | Japan | 73/597 |
| 2248824 | 10/1990 | Japan | 73/597 |

OTHER PUBLICATIONS

"Results of the Ultrasonic Examination of Reactor Internals at Connecticut Yankee", Prepared for Northeast Utilities Service Co, dated Oct. 27, 1987.

G.A. Budenkov, V.N. Kvyatkoskii, and Yu V. Petrov, "Oblique Radiation of Ultrasound by an Electromagnetic-Acoustical Method", Defektoskopia, #1, pp. 45–50 Jan.-Feb. 1973.

*Primary Examiner*—Richard Chilcot
*Assistant Examiner*—Max H. Noori
*Attorney, Agent, or Firm*—Daniel S. Kalka; Robert J. Edwards

[57] ABSTRACT

A device for measuring a load on a part and for monitoring the integrity of the part such as a bolt, comprises a socket having walls defining an interior space wherein the socket engages the bolt for transmitting a load to the bolt. An electromagnetic acoustic transducer comprising a magnet and a coil is located in the interior space of the socket near the bolt. The coil provides a current while the magnet provides a magnetic field such that the magnet and the coil generate an ultrasonic signal within the bolt. A detector is used to detect and measure a change in the ultrasonic signal at the bolt for measuring the load on the bolt and for detecting any flaws in the bolt.

14 Claims, 5 Drawing Sheets

EMAT 20
DEFECT FREE FASTENER
ULTRASONIC WAVE
2

EMAT 20
FLAWED FASTENER
ULTRASONIC WAVE
3 CRACK

60

EMAT DISPLAY SHOWING DEFECT FREE FASTENER

60

EMAT DISPLAY SHOWING REFLECTIONS FROM CRACK

FASTENER CHARACTERIZATION WITH AN ELECTROMAGNETIC ACOUSTIC TRANSDUCER

This application is a Continuation-In-Part of application Ser. No. 08/196,917 filed Feb. 15, 1994, now U.S. Pat. No. 5,499,540.

BACKGROUND OF THE INVENTION

1. Field of the Invention

The present invention relates in general to ultrasonic transducers and in particular to a new and useful method using an electromagnetic acoustic transducer for measuring the load on a bolt and providing a continuous monitor of fastener integrity by detecting cracks or flaws prior to the initiation of and/or during the loading procedure.

2. Description of the Related Art

A desired preload on a bolt is usually achieved during assembly of a structure by applying a specified torque to the bolt. It has been demonstrated that 90% of the torque applied to the bolt during assembly is used to overcome frictional forces. Small fluctuations in these frictional forces for a given fixed applied torque result in large fluctuations in the preload to the bolt. In a study of bolt preload vs. applied torque for bolts used in the construction of the Space Shuttle Orbiter, a variation in bolt preload of more than a factor of two was reported for a given applied torque. Bolts having improper preloads can lead to catastrophic failure of critical components in a wide range of applications.

Accordingly, ultrasonic methods using transducers have been developed in an effort to provide improved bolt load measurement. For example, when it was discovered that bolts used in reactor vessel internals in nuclear power plants were failing due to improper preload, an ultrasonic method was developed for setting the preload using conventional ultrasonic transducers. This method was subsequently used in the replacement of these critical bolts in the nuclear power generation facilities.

According to this method, the bolt preload is set by a precise measurement of the ultrasonic time of flight over the length of the bolt before and after tightening. While this method provides much improved bolt preload measurements compared to torque measurements, significant errors are introduced when removing and reapplying a transducer to the head of the bolt.

Using conventional ultrasonic transducers, sound waves are transmitted and received from the bolt via a coupling fluid. Because the velocity of sound in the couplant is many times slower than that of the steel, which is used in the bolt, small variations in the couplant path length can cause large variations in the transit time of the ultrasonic signal. The uncertainty introduced by the couplant path has limited most conventional ultrasonic bolt load measurements to measuring the time of arrival difference between successive echoes which assumes that the couplant path transit time is identical for each echo. There would be several advantages for only using the first echo for ultrasonic bolt preload measurements. Primarily, the first echo is generally the largest, and less affected by lack of parallelism and flatness as compared to later echoes. For example, if the end of the bolt surface is at a small angle, θ, with respect to the head of the bolt surface, the first echo arrives at the head of the bolt at an angle of 2θ while the second echo arrives at an angle of 6θ. The main drawback to these methods is that the all important application of couplant and transducer to the head of the bolt makes the automation of conventional ultrasonic bolt preload measurements a difficult task.

The usefulness of conventional ultrasonic techniques for flaw detection and material property characterization is well established. Conventional piezoelectric ultrasonic methods have been employed for detection of cracks in bolts used in nuclear power plant reactor vessel internals and supporting structures. Generation of ultrasonic waves is achieved primarily by some form of electromechanical conversion usually piezoelectricity. This method of generating ultrasound has a disadvantage in that it requires a fluid couplant to mechanically transfer sound into and out of the component being tested. The test object must be covered with a thin layer of fluid or immersed which complicates testing, often reduces the inspection rate, and can even introduce errors into the measurement. In some cases, the test may be impossible because of this requirement. Couplant clean up can be a significant problem in certain applications, and post-test corrosion of the component can be the cause of rejection in production. An ultrasonic technique that does not rely on a couplant has many advantages to offer.

SUMMARY OF THE INVENTION

The present invention pertains to a device for measuring a load on a part, such as a bolt, and also for monitoring the integrity of the part. The device comprises a socket having walls defining an interior space, wherein the socket engages the bolt for transmitting a load to the bolt. An electromagnetic acoustic transducer comprising a magnet and a coil is located in the interior space of the socket near the bolt. The coil induces eddy currents while the magnet provides a magnetic field such that the magnet and the coil together generate an ultrasonic signal directly in to the bolt. A detector is used to detect and measure a change in the transit time of the ultrasonic signal in the bolt.

The present invention also comprises a method for measuring a load on a part and for monitoring the integrity of the part. The method comprises the steps of providing a socket and engaging the socket with the part such that the interior space of the socket is provided between the socket and the part. A magnetic field is generated in the interior space of the socket; and a current is provided in the interior space of the socket such that the current and the magnetic field produce an ultrasonic signal within the part. The ultrasonic signal at the part is monitored and changes in the ultrasonic signal are detected by a detector. In this manner, the method continuously measures and controls load on the part during a torquing or fastening operation and provides a continuous monitoring of the part's integrity by detecting cracks or flaws prior to initiation of and/or during the loading procedure.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
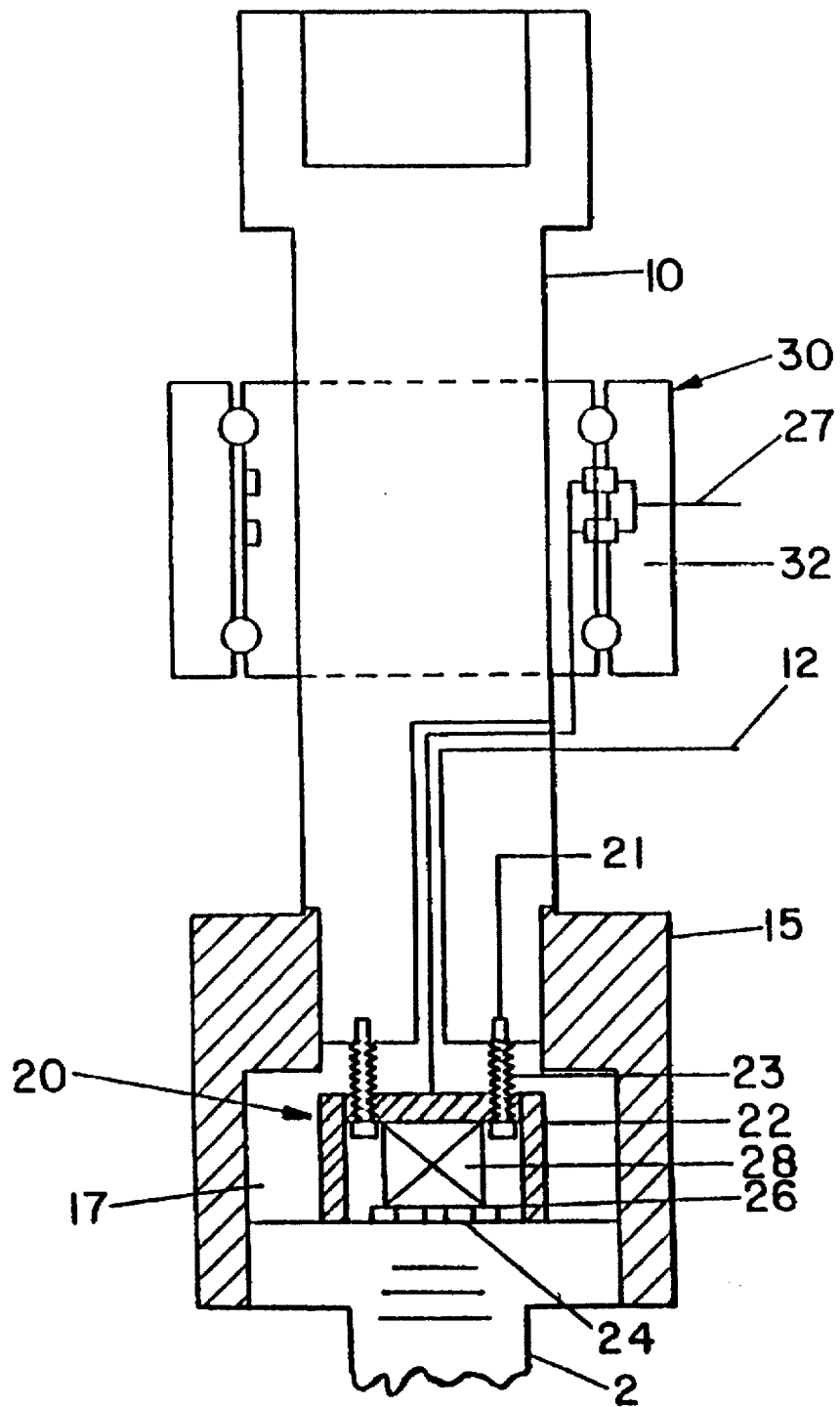
FIG. 1 is a schematic view illustrating the present invention.

The present invention is a device and method for tension and load measurement of a bolt using an electromagnetic acoustic transducer. The present invention in conjunction with the tension and load measurement of the fastener also provides a continuous monitor of fastener integrity by detecting cracks or flaws prior to the initiation of and during the loading procedure. Further, the present invention may be employed to verify that the proper fastener material including the right alloy and heat treatment condition has been employed in a particular application. The present invention comprises an electromagnetic acoustic transducer (EMAT) which generates and receives ultrasonic waves without the need to contact the material of a part such as a fastener like a bolt, in which the ultrasonic waves travel. The device according to the present invention, as shown in FIG. 1, is used in conjunction with a bolt 2 and comprises a socket 15 having an interior space 17. The socket 15 engages the bolt 2 for tensioning the bolt 2 and placing a load thereon. The interior space 17 of the socket 15 is located between the bolt 2 and the socket 15. A socket drive 10 is used in conjunction with the socket 15; and the socket drive 10 is detachably engageable with the socket 15 for changing to different size sockets for accommodating different sized bolts 2.

An electromagnetic transducer assembly 20 is located within the interior space 17 of the socket 15 at the bolt 2. The EMAT assembly 20 comprises a housing 22 and a wearplate 24 which contacts the bolt 2. Within the housing 22 and the wearplate 24 is located a permanent magnet 28 for producing a magnetic field and a coil 26 for providing a current. The EMAT assembly 20 is connected to the socket drive 10 by attachment bolts 21 and springs 23. A cable 27 is connected to the coil 26 for providing the current to the coil 26. The cable 27 is channeled to the coil 26 through a cable routing hole 12 located within the socket drive 10. The cable 27 is connected to the socket drive 10 by a slip ring assembly 30 engaged around the socket drive 10. The slip ring assembly 30 comprises slip ring brushes 32.

The electromagnetic transducer assembly 20 is used as a generator of ultrasonic waves by locating the coil 26 in a uniform magnetic field produced by a permanent magnet 28 or an electromagnet such that the ultrasonic waves are provided near the surface of the metal bolt 2. By transformer action, a surface current is introduced into the metal bolt 2. This surface current in the presence of the magnetic field experiences a Lorentz force which produces oscillating surface stresses. On reception, the surface of the metal 2 oscillates in the magnetic field thereby inducing a voltage in the coil 26. The transduction process takes place within an electromagnetic skin depth, which for materials such as steel or aluminum, at megahertz frequencies, is a fraction of a mil. An alternate mechanism generally employed with EMATs to generate and receive the ultrasound is magnetostriction. The magnetostriction mechanism involves generating and receiving ultrasound in ferromagnetic materials through magnetic interactions. When a magnetic field is applied to a ferromagnetic material, the material experiences an internal stress. This process is known as magnetostriction. The mount of stress generated depends on the magnitude of the magnetic field and the properties of the material. EMATs are employed for ferromagnetic materials where a static or quasi static magnetic field is applied to the ferromagnetic material to bias the material into a region where a small change in magnetic field produces a large change in stress. An RF (radio frequency) coil is then driven with an RF channel burst to set up RF magnetic fields in the surface of the material. The RF fields set up stresses in the material surface which launch ultrasound into the material. Ultrasound is detected by a reciprocal process. With either mechanism the received signal strength falls off exponentially with increasing gap between the EMAT coil and the metal surface.

The present invention provides a very reproducible non-contact system for generating and detecting ultrasound. Because the current of the EMAT coil 26 directly generates ultrasonic waves in the surface of the bolt 2, the precise time of flight measurements can be made by timing from the current pulse to the first reflection which eliminates many of the problems associated with known, conventional ultrasonic measuring devices.

Due to the development of the present invention, some of the problems that have been associated with previous efforts to measure bolt loading by ultrasonic methods have been minimized or eliminated. The EMAT of the present invention generates and receives ultrasonic waves without the need to contact the material in which the waves are traveling. This eliminates the requirement for a liquid couplant between the transducer and the material under test, which is the source of significant error and problems for automating the measurement process.

In operation, the EMAT sensor 20 rotates with the socket 15 and the bolt 2. Ultrasonic signals are transmitted and received via the slip rings 32 while testing the bolted joint 2. Alternatively, the transducer cable 27 is allowed to twist during the bolt tightening.

Figure 2:
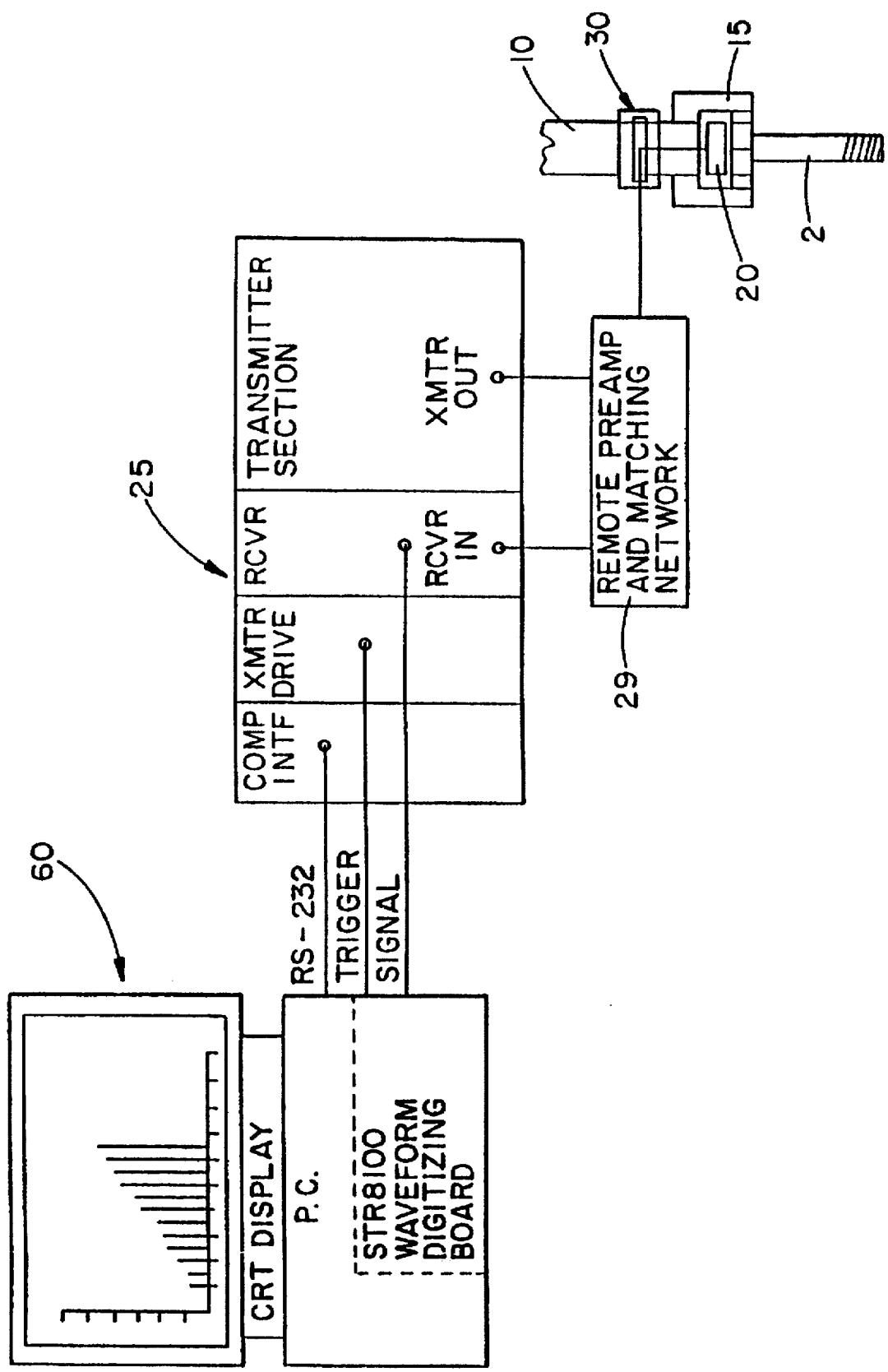
FIG. 2 is a schematic view illustrating the present invention used in conjunction with a detector and a monitor.

FIG. 2 shows EMAT instrumentation and computer 25 comprising a display means 60 and a remote amp and matching network 29 which electrically matches the EMAT coil 26 and cable 27 to the EMAT instrumentation 25. The detector 25, is a computer which takes measurements on the unloaded bolt 2 in order to establish a base line, and then measures and plots the bolt load while tightening the bolt 2.

As shown in FIG. 1, the EMAT sensor 20 is spring loaded by springs 23 so that the sensor 20 is automatically seated on the head of a bolt 2 as soon as the socket 15 is placed on the bolt head 2. The EMAT sensor 20 is attached to the drive assembly 10 in such a manner so that several different bolt sizes can be accommodated by changing sockets 15. EMAT measurements are taken as follows: prior to loading, i.e. on an unloaded bolt, continuously during the loading of the bolt, and after the loading of the bolt. When the desired load has been reached, the sensor 20 does not have to be removed. This eliminates the errors previously encountered in known transducers which are caused by having to attach and remove the ultrasonic transducers for the two tests, i.e. the preload test and the postload test. The method according to the present invention is well suited for automotive bolt tightening for use in production lines and various robotic applications.

It is well known that commercial ultrasonic bolt load measurement devices have been found to produce highly variable results primarily due to couplant variability.

Additionally, the repeatability of the EMAT method according to the present invention for measurements spaced over a period of time is much better than that of conventional ultrasonic methods. It may be desirable to measure the load of a bolt periodically to ensure that it is still within specifications. Because the EMAT 20 operates without couplant, re-application of the sensor 20 to make periodic measurements produces results with good accuracy if the load is unchanged.

Figure 3:
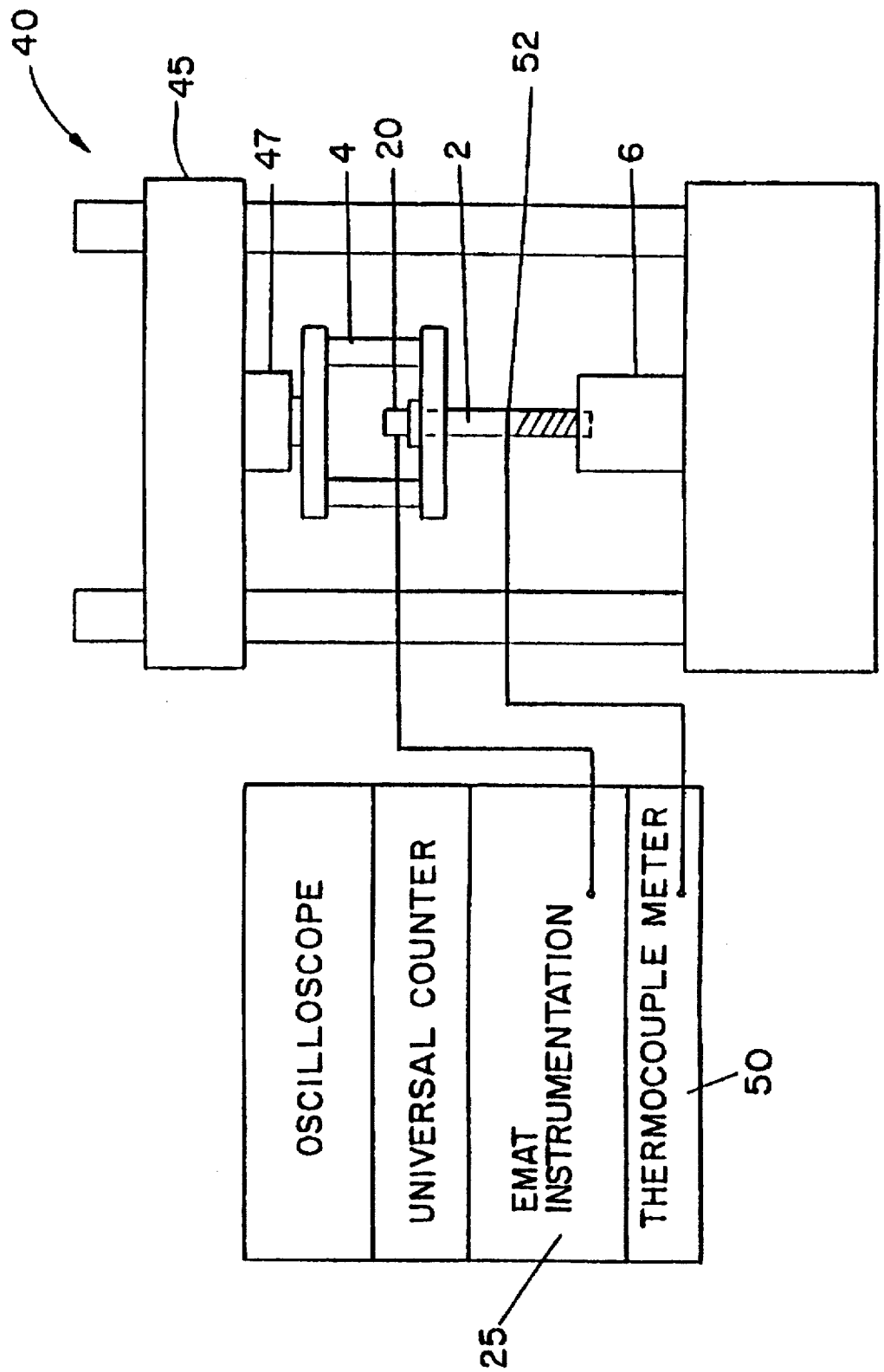
FIG. 3 is a schematic view illustrating a bolt tension test set-up utilizing the present invention.
Figure 4:
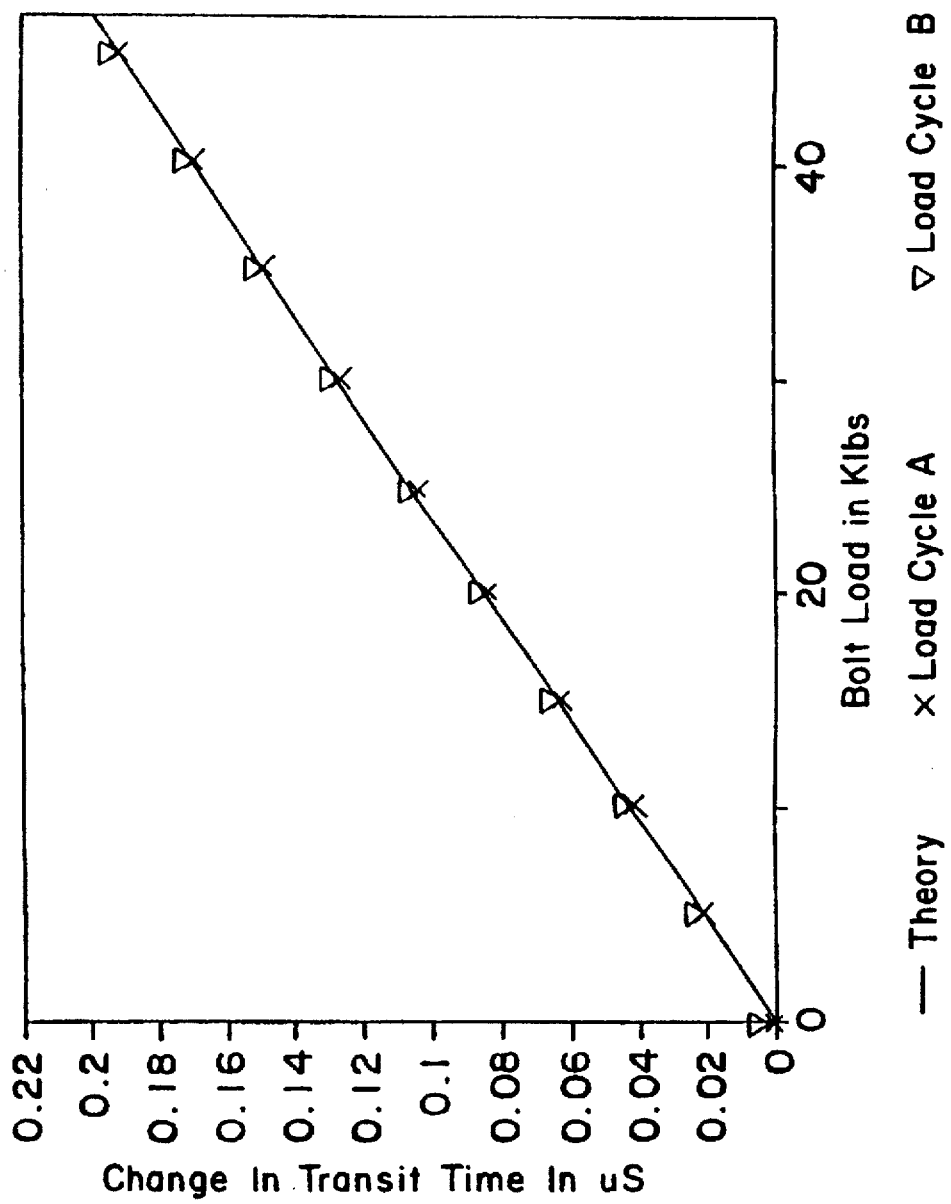
FIG. 4 is a graph plotting a change in transit time vs. bolt load.

A preliminary study of the novel concept of the present invention of using an EMAT for measuring bolt loading was first conducted under laboratory conditions. FIG. 3 shows an experimental set-up used during the preliminary study. A tension test set-up 40 was used in conjunction with a bolt loading fixture 4 and 6 and a 50,000 pound loading frame comprising a load device 45. A specimen bolt 2 was loaded in the tension test set-up 40 at 5,000 pound increments and measurements of arrival time, load cell output, from load cell 47, and bolt temperature were recorded. The results of the measuring times for the transmitter current pulse to first echo are illustrated in FIG. 4 for two successive load cycles.

The effect on the accuracy of the readings caused by removing and replacing the transducer was tested by removing and replacing the transducer on the head of the unstressed bolt six times. The maximum variation in the time of flight was 4 nS, or an error corresponding to about 1.5% of the recommended load value. The average variation was only 1.2 nS, or less than 0.5% of the applied load. These results were unexpected since the experimental transducer was not very rugged and indicates that the transducer can be easily removed and replaced without introducing significant errors in bolt preload measurements. The ability to remove and replace the transducer without introducing significant errors allows for the reloading of a bolt in an assembly where preload can change.

FIGS. 5-8 show the manner where the EMAT assembly 20 located within the socket (not shown) can also be used to provide a continuous monitor of fastener integrity by detecting cracks or flaws prior to the initiation of and during the loading procedure. Furthermore, the EMAT assembly 20 can also be employed to verify that the proper fastener material, alloy and heat treatment condition is being used for a particular application. These material properties influence ultrasonic velocity/attenuation. The fastener material 2 may be verified as soon as the sensor assembly 2 is positioned on the fastener 2 prior to load monitoring. The term "fastener" as used herein is meant to include a bolt, a screw, a rivet, or any other fastener.

Figure 5:
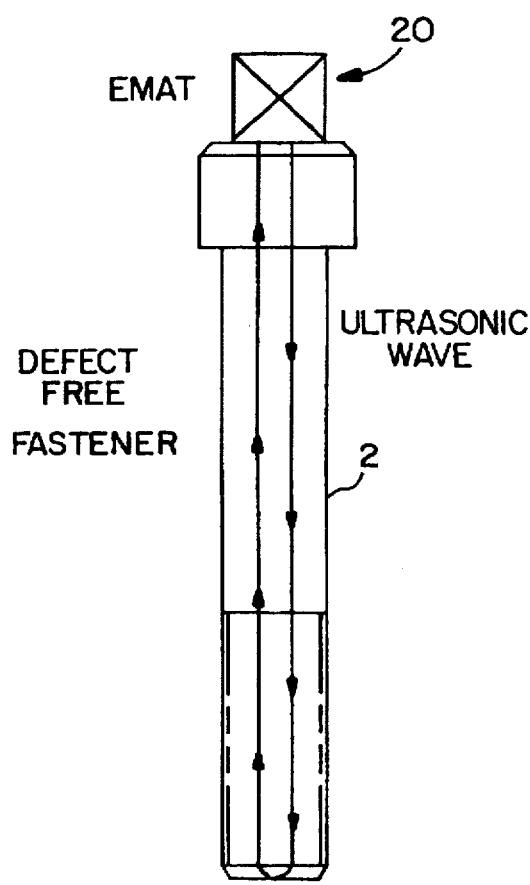
FIG. 5 is a cross-section of a defect free fastener with an EMAT illustrating the path of an ultrasonic wave.
Figure 7:
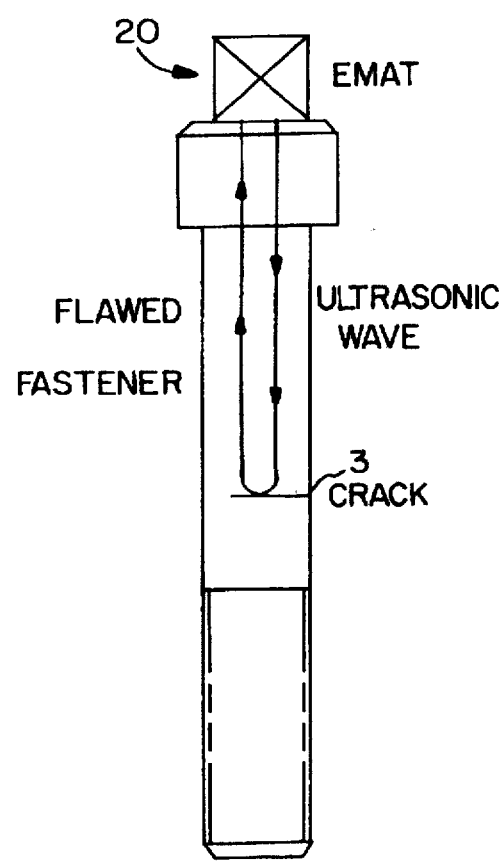
FIG. 7 is a cross-section of a flawed fastener with an EMAT illustrating the path of an ultrasonic wave.
Figure 6:
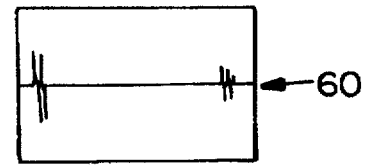
FIG. 6 is an EMAT display showing the defect free fastener.
Figure 8:
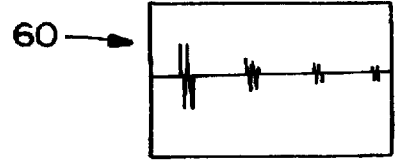
FIG. 8 is an EMAT display showing reflections from the crack in the fastener shown in FIG. 7.

In FIGS. 5-8, there is shown an EMAT generated ultrasonic wave and the manner in which it propagates through a defect free fastener in FIG. 5 and a flawed fastener in FIG. 7. Since EMAT ultrasonic generation is so material dependent (electrical resistivity, magnetic permeability, density, etc.) the placement of the EMAT on the surface of the fastener will provide immediate verification that each fastener is correct in terms of material, alloy and heat treatment. After EMAT placement and material verification, if the ultrasound wave strikes an object in the form of a crack or inhomogeneity, part of the energy will (depending on the size and orientation of the flaw or reflector) be reflected back to the receiver of the EMAT assembly 20 and the remainder will travel further into the fastener 2 eventually reflecting off the back wall or end of the fastener. FIG. 7 illustrates this for a crack 3. The signals from the receiver of EMAT assembly 20 are displayed as peaks on a base line of the cathode ray tube display as shown in FIGS. 6 and 8 for a defect free and flawed fastener respectively. The horizontal sweep is proportional to time so the transit times of the ultrasonic wave to and from the flaw or reflector, and to and from the back wall correspond respectively to the distances on the screen from the initial peak to the echo peak corresponding to the reflector and back wall.

By calibration of the display instrument time base in time per unit length, the transit time to the end of the fastener can be clearly shown, and any crack or other flaw will act as a reflector and cause an echo or indication on the EMAT display located between the initial pulse and the back wall (bolt end).

An advantage of the present invention is that the EMAT assembly is used to simultaneously measure and/or control the loading or tightening operation, confirm and monitor integrity by detecting flaws to eliminate using a defective bolt in production as well as verify material, alloy, and heat treatment condition as simply as placing the fastening device on the fastener.

While a specific embodiment of the invention has been shown and described in detail to illustrate the application of the principles of the invention, it will be understood that the invention may be embodied otherwise without departing from such principles.

What is claimed is:

1. A device for measuring a load on a fastener and for monitoring the integrity of the fastener, the device comprising:

means for engaging the fastener, said engaging means having an interior space, the interior space of the engaging means being located between the engaging means and the fastener;

drive means for transmitting a load to the fastener through said engaging means, said drive means being detachably engageable with said engaging means;

a coil located in the interior space near the fastener for introducing an eddy current in the fastener;

means for providing current to said coil;

a magnet engaging the coil in the interior space and being attached to said drive means for providing a magnetic field, the magnet and the coil generating a noncontact ultrasonic signal in the fastener;

detection means for measuring time of flight and detecting a change in the ultrasonic signal provided to the fastener; and display means for showing any change in the ultrasonic signal indicative of a flaw.

2. The device according to claim 1, wherein said engaging means comprises a socket.

3. The device according to claim 1, wherein said display means compares the ultrasonic signal with a calibrated signal for verifying material, alloy and heat condition treatment.

4. The device according to claim 2, including a housing located in the interior space and a wearplate for contacting the fastener, the coil and the magnet being connected to the housing, and connecting means for connecting the housing to the drive means.

5. The device according to claim 4, wherein the connecting means comprises a bolt connected to the housing and the drive means.

6. The device according to claim 5, wherein the connecting means further comprises a spring between the housing and the drive means.

7. The device according to claim 1, including a cable connected to the coil and the detection means.

8. The device according to claim 7, wherein the drive means includes an aperture for channeling the cable to the coil.

9. The device according to claim 8, including retaining means for electrically connecting the cable to the coil.

10. The device according to claim 9, wherein the retaining means comprises a slip ring assembly engaged with the drive means.

11. A method for measuring a load on a fastener and for monitoring the integrity of the fastener, the method comprising the steps of:

providing means for engaging a fastener, the engaging means having walls defining an interior space;

engaging the fastener such that the interior space is provided between the engaging means and the fastener;

transmitting a load to the fastener with drive means through the engaging means, the drive means being detachably engageable with the engaging means;

attaching a magnet with a coil to the drive means so that the magnet and coil are positioned in the interior space of the engaging means;

generating a magnetic field in the interior space of the engaging means;

providing a current in the interior space such that the current and the magnetic field produce a noncontact ultrasonic signal in the fastener;

measuring time of flight of the ultrasonic signal in the fastener;

detecting a change in the ultrasonic signal; and displaying any change in the ultrasonic signal indicative of a flaw.

12. The method according to claim 11, wherein the engaging means comprises a socket.

13. The method according to claim 11, further comprising the step of comparing the ultrasonic signal with a calibrated signal for verifying material, alloy and heat treatment condition for the fastener.

14. The method according to claim 11, including rotating the socket and the fastener.

* * * * *